United States Patent [19]

Naylor

[11] Patent Number: 4,701,412

[45] Date of Patent: * Oct. 20, 1987

[54] METHOD AND APPARATUS FOR PREVENTING CROSS-EXAMINATION OF BIOCHEMICAL TEST WELLS IN A MICROTITER TEST PLATE

[75] Inventor: Harry B. Naylor, Bellingham, Wash.

[73] Assignee: Pasco Laboratories, Inc., Wheatridge, Colo.

[ * ] Notice: The portion of the term of this patent subsequent to Jul. 14, 2004 has been disclaimed.

[21] Appl. No.: 835,190

[22] Filed: Mar. 3, 1986

Related U.S. Application Data

[63] Continuation-in-part of Ser. No. 723,360, Apr. 15, 1985.

[51] Int. Cl.$^4$ ............................................. C12Q 1/24
[52] U.S. Cl. ..................................... 435/30; 435/301; 423/237
[58] Field of Search ................................... 435/30–32, 435/287, 297–301, 810; 422/56, 61, 101, 102; 55/524; 423/237, 238

[56] References Cited

U.S. PATENT DOCUMENTS

| | | | |
|---|---|---|---|
| 3,438,737 | 4/1969 | Atkinson | 422/56 |
| 3,873,269 | 3/1975 | Kraffczyk et al. | 422/56 |
| 4,070,300 | 1/1978 | Moroni et al. | 423/237 |
| 4,080,423 | 3/1978 | Smith et al. | 423/238 |

Primary Examiner—Samuel Scott
Assistant Examiner—Noah Kamen
Attorney, Agent, or Firm—Edwin J. Spangler, Jr.

[57] ABSTRACT

This invention relates to an improved method and apparatus for preventing cross-contamination of biochemical test wells included in a microtiter test plate which comprises the covering of the biochemical test wells with a porous barrier that has been impregnated with an approximately 10% (W/V) solution of a solid, water soluble compound and then dried before use, the impregnating material being one selected form a group of chemical compounds consisting of inorganic acid phosphates, the acid salts of amino acids and the polycarboxylic organic acids which are relatively non-volatile, non-hygroscopic and non-toxioc to humans and bacteria while remaining effective to neutralize alkaline gases without attacking the barrier material.

5 Claims, No Drawings

METHOD AND APPARATUS FOR PREVENTING CROSS-EXAMINATION OF BIOCHEMICAL TEST WELLS IN A MICROTITER TEST PLATE

This is a continuation-in-part of my copending application Ser. No. 723,360 filed Apr. 15, 1985 in which I disclosed a method for neutralizing volatile alkaline products evolved through bacterial growth taking place in the wells of a combined biochemical identification-antiobiotic microtiter test plate, thus preventing false biochemical test results due to cross-contamination with the volatile alkaline products which consisted of impregnating a porous barrier with an acidic compound capable of neutralizing the alkaline products and then covering the test wells with such a barrier. At the time, I discovered that potassium dihydrogen phosphate was an ideal acidic compoun for impregnation of the test well barrier and it continues to be one of the best, if not, in fact, the best one to use. It possesses all the properties I have found desirable in the acidic compound to be used for this purpose such as, for example, those which follow.

Ideally, the acidic compound which will be effective as an impregnate for the test well barrier should be readily soluble in water (at least 10% W/V) at or near ambient temperatures. Obviously, it should possess the ability to quickly and easily neutralize alkaline gases like ammonia while at the same time having a low toxicity for both humans and bacteria. Low volatility and being relatively non-hygroscopic are other desirable properties as well as that of not attacking the barrier material.

Bearing in mind the aforementioned properties, certain acidic compounds can be eliminated at the outset. For instance, strong acids like hydrochloric, nitric and sulfuric, in addition to being liquids under normal conditions of pressure and temperature, would have a damaging effect on the filter paper or other porous barrier. Hydrochloric acid is also too volatile to be of any use since it would evaporate while the barrier impregnated therewith was being dried. Other acids like hydrocyanic are too toxic for both humans and many types of bacteria to be practical. Other acids, such as boric, oxalic, and 5-sulfosalicylic, for example, are too irritating to the skin and mucous membranes to receive serious consideration. Acids such as adipic, salicylic, phthalic, and others of this type have a rather low solubility in water. Consequently, it would not be possible to impregnate the barrier with a sufficient concentration thereof to effectively neutralize the evolved alkaline products even though they would meet the other standards. Those acidic compounds that are highly hygroscopic in the dehydrated form like, for instance, glycine hydrochloride, should not be used since they pick up water from the test wells and form droplets that can fall back into the well giving false positive acid reactions and false negative alkaline reactions. Last, but by no means least, are the considerable number of acidic compounds such as acetic acid, propionic acid, butyric acid and the like which, while otherwise suitable, are either in the gaseous or liquid form at normal temperatures and pressures and, therefore, unsuitable because they cannot be used in the preparation of dry barriers that can be handled conveniently.

I have now discovered that, despite the several varied and distinctive properties that a suitable acidic impregnate should possess, there are several other acidic compounds in addition to sodium or potassium acid phosphate which are capable of neutralizing the alkaline products evolved by reasons of the bacterial growth taking place in the test wells of a microtiter test plate. For example, I have been able to show that, in addition to the inorganic acid phosphates, the acid salts of amino acids perform quite well as do the polycarboxylic and sulfonated organic acids.

It is, therefore, the principal object of the present invention to provide a broadened class of acidic compounds which can be satisfactorily impregnated into a porous medium and used to neutralize alkaline products evolved by bacterial growth taking place in the wells of a microtiter test plate, the presence of which would otherwise contaminate the biochemical test wells and possibly result in both false-positive and false-negative test results.

A second objective is the provision of acidic compounds of the class aforementioned which are essentially non-toxic to both humans and the bacteria growing in the wells.

Another object of the invention herein disclosed and claimed is one of providing a select group of compounds for the aforementioned purpose which are sufficiently soluble such that a quantity thereof in excess of that required to neutralize the volatile alkaline products evolved can be impregnated into the porous medium and remain there after it is dried.

Still another objective is to provide an acidic compound which, in dehydrated form, is non-hygroscopic to the extent that it is incapable of absorbing enough water from the suspension in the test well to produce a contaminated droplet on the underside of the acid-impregnated barrier that can drop off and reenter the well.

An additional object is to provide a group of chemical compounds for neutralizing volatile alkaline products that are water-soluble dry solids at ordinary temperatures and pressures and, therefore, can be dissolved in water and impregnated into a porous paper matte or similar material and dried without losing activity.

Further objects of the present invention are to provide a number of acidic compounds useful in the neutralization of volatile alkaline products that are readily obtainable on the open market, safe to handle, have a good shelf life and are not so strong as to destroy or even damage the porous material into which they are introduced.

Other objects will be in part apparent and in part pointed out specifically hereinafter in connection with the detailed description which follows.

I found that, in my attempt to select acidic compounds which satisfied the several criteria mentioned above that would be required of the ideal impregnate to neutralize volatile alkaline products evolved by bacterial growth in microtiter and biochemical test wells, there were, as a matter of fact, very few possibilities. Those I selected for testing were as follows:

1. Boric acid
2. Oxalic acid
3. 5-Sulfosalicylic acid
4. Potassium acid phthalate
5. Glycine hydrochloride
6. Cysteine hydrochloride
7. Bis-tris buffer (effective pH range 5.8 to 7.2)
8. Mes buffer (effective pH range 5.5 to 6.7)
9. DL Malic acid
10. Malonic acid
11. DL Tartaric acid 12. Citric acid Even some of the above acidic compounds possess one or more undesirable properties such as, for example, low solubility; yet, I tested them anyway.

The initial tests were run using 10% (W/V) solutions except for potassium acid phthalate (8%), boric acid (5%) and oxalic acid (9%) due to the limited solubility of the latter compounds. The porous member chosen for impregnation was Whatman #1 filter paper cut into rectangles sized to cover the so-called "gram-negative" biochemical test wells in a minimum inhibitory concentration (MIC)identification microplate. Inocula were prepared according to the generally accepted procedure for MIC plates to be used for antibiotic susceptibility testing. The following test organisms were used as the inocula in the tests although not all were necessarily tested in each experiment:

1. *Pseudomonas aeruginosa*
2. *Citrobacter freundii*
3. *Aeromonas caviae*
4. *Pasteurella aerogenes*
5. *Acinetobacter anitratus*
6. *Providencia alcalifaciens*
7. *Klebsiella pneumoniae*
8. *Proteus mirabilis*

All of the tests performed utilized *Pseudomonas aeruginosa* as the inoculum in all of the MIC wells because of its capacity to produce ammonia along with its resistance to most of the antibiotics. All of the biochemical test wells were then inoculated with one of the test organisms listed above. A strip impregnated with a 15% potassium dihydrogen phosphate solution was placed over the biochemical test wells of a second plate and the experimental test strips were used on the additional plates. Since it is well known that certain tests must be conducted under anaerobic conditions, the medium contained in these wells was covered with mineral oil in accordance with accepted practice. Specifically, the oxidation-fermentation of glucose test well; the wells for testing the decarboxylation of arginine, lysine, and ornithine; and the well for detecting urease activity are usually covered. In these experiments, the oxidation-fermentation of glucose well was always covered with oil while the other wells mentioned above were sometimes covered with oil and sometimes not. Since ammonia will cause false positive reactions in the unprotected decarboxylase and urease test wells, the mineral oil was omitted with some of the test organisms in order to put the barrier strips to a more critical test.

All of the plates were incubated at 36° C. for 18 to 22 hours before the first evaluation was made. The same impregnated barriers were then replaced on the plates and they were again observed after a total incubation time of approximately 40 to 42 hours. Prolonged incubation is sometimes necessary in order to properly identify the test organism. In my experiments, however, I subjected the plates to prolonged incubation for the specific purpose of determining which of the protective strips would remain effective for the longest time.

Results of the tests were evaluated on the basis of comparisons of the reactions that the organisms tested were known to produce with conventional tests, i.e. using other than microtiter test plates; the reactions observed using microplates with unprotected biochemical test wells; and those in which the biochemical test wells were covered with the neutralizing barriers impregnated with the acidic compounds being evaluated. Barrier strips impregnated with potassium dihydrogen phosphate were included because I had already thoroughly tested this neutralizing agent and knew it to be quite effective; therefore, it provided me with a standard against which to evaluate the effectiveness of the other compounds being tested.

In the tables which follow, abbreviations are used to identify the various biochemical substrates and they are:

| Abbr. | Substrate | Abbr. | Substrate |
|---|---|---|---|
| OF/G | Fermentation of Glucose | GLU | Glucose |
| MAN | Mannitol | ARA | Arabinose |
| TRE | Trehalose | CEL | Cellobiose |
| SOR | Sorbitol | MEL | Melibiose |
| SUC | Sucrose | RAF | Raffinose |
| RHA | Rhamnose | ADO | Adonitol |
| ARG | Arginine | LYS | Lysine |
| ORN | Ornithine | URE | Urea |
| CIT | Citrate | MAL | Malonate |

Also, as previously noted, two of the acidic compounds tested were MES buffer and BIS-TRIS buffer. The MES buffer is (2 [N-Morpholine] ethanesulfonic acid, whereas, the BIS-TRIS buffer is [Bis (2-hydroxyethyl) imino tris (hydroxymethyl) methane.

TABLE I

| | Test Organism - *Acinetobacter anitratus* | | |
|---|---|---|---|
| Incubation Time | No Barrier | KH$_2$PO$_4$ (15%) | Tartaric Acid (10%) |
| *23 hours | False neg. on ARA, CEL, MEL and RHA | Okay | Okay |
| *42 hours | False neg. on GLU, ARA, CEL, MEL and RHA | +/− on CEL | False neg. on CEL |

TABLE II

| | Test organism - *Acinetobacter anitratus* | | |
|---|---|---|---|
| Incubation Time | No Barrier | KH$_2$PO$_4$ (15%) | 5-Sulfosalicylic Acid (10%) |
| *23 hours | False neg. on ARA, CEL, MEL and RHA | Okay | Okay |
| *42 hours | False neg. on GLU, ARA, CEL, MEL AND RHA | +/− on CEL | False neg. on CEL |
| **19½ hours | False neg. on ARA and CEL False pos. on ARG, LYS, ORN and URE | False pos. on ARG, LYS and ORN | False pos. on ARG, LYS and ORN |
| **42 hours | False neg. on GLU, ARA, CEL, MEL and RHA False pos. on ARG, LYS, ORN and URE | +/− on CEL False pos. on LYS | False pos. on LYS |

*These tests were conducted with the OF/G, ARG, ORN, LYS and URE wells oiled with mineral oil.
**These tests were conducted with only the OF/G wells oiled with mineral oil.

TABLE III

| | Test organism - *acinetobacter anitratus* | | |
|---|---|---|---|
| Incubation Time | No Barrier | KH$_2$PO$_4$ (15%) | Malic Acid (10%) |
| *21 hours | False neg. on CEL +/− on MEL | Okay | Okay |
| *41 hours | False neg. on GLU, ARA, CEL, | +/− on CEL and GLU | +/− on CEL |

TABLE III-continued

| | Test organism - acinetobacter anitratus | | |
|---|---|---|---|
| Incubation Time | No Barrier | KH₂PO₄ (15%) | Malic Acid (10%) |
| | MEL and RHA | | |

*These tests were conducted with the OF/G, ARG, ORN, LYS and URE wells oiled with mineral oil.

TABLE IV

| | Test organism - acinetobacter anitratus | | |
|---|---|---|---|
| Incubation Time | No Barrier | KH₂PO₄ (15%) | Malonic Acid (10%) |
| *21 hours | False neg. on CEL +/− on MEL | Okay | Okay |
| *41 hours | False neg. on GLU, ARA, CEL, MEL and RHA | +/− on CEL | Okay |
| **19½ hours | False neg. on ARA and CEL False pos. on ARG, LYS, ORN and URE | False pos. on ARG, LYS and ORN | False pos. on ARG, LYS and ORN |
| **42 hours | False neg. on GLU, ARA, CEL, MEL and RHA False pos. on ARG, LYS, ORN and URE | +/− on CEL False pos. on LYS | False pos. on LYS |

TABLE IV-continued

| | Test organism - acinetobacter anitratus | | |
|---|---|---|---|
| Incubation Time | No Barrier | KH₂PO₄ (15%) | Malonic Acid (10%) |
| **19 hours | False neg. on CEL +/− on ARA False pos. on ARG, ORN and URE | False pos. on ARG and ORN | False pos. on ARG and ORN |
| **42 hours | False neg. on GLU, ARA and MEL False pos. on ARG, ORN and URE | Okay | Okay |
| **19½ hours | False neg. on CEL +/− on ARA and MEL False pos. on ARG, ORN and URE | False pos. on ARG and ORN | False pos. on ARG and ORN |
| **41 hours | False neg. on GLU, ARA, MEL CEL and RHA False pos. on ARG, ORN and URE | False neg. on CEL | False neg. on CEL |

*These tests were conducted with the OF/G, ARG, ORN, LYS and URE wells oiled with mineral oil.
**These tests were conducted with only the OF/G wells oiled with mineral oil.

TABLE V

| | Test Organism - acinetobacter anitratus | | |
|---|---|---|---|
| Incubation Time | No Barrier | KH₂PO₄ (15%) | Oxalic Acid (9%) |
| *21 hours | False neg. on CEL +/− on MEL | Okay | Okay |
| *41 hours | False neg. on GLU, ARA, CEL MEL and RHA | +/− on GLU and CEL | False neg. on CEL +/− on GLU |

TABLE VI

| | Test Organism - acinetobacter anitratus | | |
|---|---|---|---|
| Incubation Time | No Barrier | KH₂PO₄ (15%) | Cysteine.HCl 10% |
| **19½ hours | False neg. on ARA and CEL False pos. on ARG, LYS, ORN and URE | False pos. on ARG, LYS and ORN | False pos. on ARG, LYS and ORN |
| **42 hours | False neg. on GLU, ARA, CEL MEL and RHA False pos. on ARG, LYS, ORN and URE | +/− on CEL False pos. on LYS | False neg. on CEL +/− on GLU, RHA and ORN False pos. on LYS |

*These tests were conducted with the OF/G, ARG, ORN, LYS and URE wells oiled with mineral oil.
**These tests were conducted with only the OF/G wells oiled with mineral oil.

TABLE VII

| | Test Organism - acinetobacter anitratus | | |
|---|---|---|---|
| Incubation Time | No Barrier | KH₂PO₄ (15%) | Glycine.HCl 10% |
| **19½ hours | False neg. on CEL +/− on ARA and MEL False pos. on ARG, ORN and URE | False pos. on ARG and ORN | False pos. on ARG and ORN |
| **41 hours | False neg. on GLU, ARA, MEL CEL and RHA False pos. on ARG, ORN and URE | False neg. on CEL | False neg. on GLU and CEL |

TABLE VIII

| | Test organism - *pasteurella aerogenes* | | |
|---|---|---|---|
| Incubation Time | No Barrier | KH$_2$PO$_4$ (15%) | 5-Sulfosalicylic Acid 10% |
| **19¼ hours | False neg. on GLU and ARA +/− on SUC False pos. on ARG, LYS, ORN, CIT and MAL | Okay | Okay |
| **42 hours | False neg. on GLU, ARA and SUC False pos. on ARG, LYS, ORN, CIT and MAL | False neg on SUC +/− on GLU False pos. on MAL +/− on ORN | False neg. on GLU and SUC |

**These tests were conducted with only the OF/G wells oiled with mineral oil.

TABLE IX

| | Test organism - *pasteurella aerogenes* | | |
|---|---|---|---|
| Incubation Time | No Barrier | KH$_2$PO$_4$ (15%) | Malic Acid 10% |
| *21 hours | False neg. on GLU, ARA and SUC False pos. on CIT and MAL | Okay | Okay |
| *41 hours | False neg. on GLU, ARA and SUC False pos. on CIT and MAL | False neg. on GLU and ARA False pos. on MAL | +/− on GLU and SUC |

*These tests were conducted with the OF/G, ARG, ORN, LYS and URE wells oiled with mineral oil.

TABLE X

| | Test organism - *pasteurella aerogenes* | | |
|---|---|---|---|
| Incubation Time | No Barrier | KH$_2$PO$_4$ (15%) | Malonic Acid (10%) |
| *21 hours | False neg. on GLU, ARA and SUC False pos. on CIT and MAL | Okay | Okay |
| *41 hours | False neg. on GLU, ARA and SUC False pos. on CIT and MAL | False neg. on GLU and SUC False pos. on MAL | Okay |
| **19½ hours | False neg. on GLU and ARA +/− on SUC False pos. on ARG, LYS, ORN, CIT and MAL | Okay | Okay |
| **42 hours | False neg. on GLU, ARA and SUC False pos. on ARG, LYS, ORN, CIT and MAL | False neg. on SUC +/− on GLU False pos. on MAL +/− on ORN | Okay |
| **19½ hours | False neg. on ARA and SUC +/− on GLU False pos. on ARG, LYS, ORN, CIT and MAL | Okay | Okay |
| **41 hours | False neg. on GLU, ARA and SUC False pos. on ARG, LYS, ORN, CIT and MAL | +/− on MAL False pos. on ORN | Okay |

*These tests were conducted with the OF/G, ARG, ORN, LYS and URE wells oiled with mineral oil.
**These tests were conducted with only the OF/G wells oiled with mineral oil.

TABLE XI

| | Test organism - *pasteurella aerogenes* | | |
|---|---|---|---|
| Incubation Time | No Barrier | KH$_2$PO$_4$ (15%) | Oxalic Acid (9%) |
| *21 hours | False neg. on GLU, ARA and SUC False pos. on CIT and MAL | Okay | Okay |
| *41 hours | False neg. on GLU, ARA and SUC False pos. on CIT and MAL | False neg. on GLU and SUC False pos. on MAL | +/− on GLU |

TABLE XII

| | Test organism - *pasteurella aerogenes* | | |
|---|---|---|---|
| Incubation Time | No Barrier | KH$_2$PO$_4$ (15%) | Cysteine.HCl (10%) |
| **19½ hours | False neg. on GLU and ARA +/− on SUC False pos. on ARG, LYS, ORN, CIT and MAL | Okay | Okay |
| **42 hours | False neg. on GLU, ARA and SUC False pos. on ARG, LYS, ORN, | False neg on SUC +/− on GLU False pos. on MAL +/− on ORN | False neg. on GLU and SUC False pos. on MAL and ORN |

TABLE XII-continued

Test organism - *pasteurella aerogenes*

| Incubation Time | No Barrier | KH₂PO₄ (15%) | Cysteine.HCl (10%) |
|---|---|---|---|
| | CIT and MAL | | |

*These tests were conducted with the OF/G, ARG, ORN, LYS and URE wells oiled with mineral oil.
**These tests were conducted with only the OF/G wells oiled with mineral oil.

TABLE XIII

Test organism - *pasteurella aerogenes*

| Incubation Time | No Barrier | KH₂PO₄ (15%) | Glycine.HCl (10%) |
|---|---|---|---|
| **19½ hours | False neg. on ARA and SUC +/− on GLU False pos. on ARG, LYS, ORN, CIT and MAL | Okay | Okay |
| **41 hours | False neg. on GLU, ARA and SUC False pos. on ARG, LYS, ORN, CIT and MAL | +/− on MAL False pos. on ORN | False neg. on GLU +/− on SUC |

TABLE XIV

Test organism - *providencia alcalifaciens*

| Incubation Time | No Barrier | KH₂PO₄ (15%) | Malic Acid (10%) |
|---|---|---|---|
| *21 hours | False neg. on ADO +/− on GLU False pos. on CIT and MAL | Okay | Okay |
| *41 hours | False neg. on ADO False pos. on MAL | False pos. on MAL | Okay |

*These tests were conducted with the OF/G, ARG, ORN, LYS and URE wells oiled with mineral oil.
**These tests were conducted with only the OF/G wells oiled with mineral oil.

TABLE XV

Test organism - *providencia alcalifaciens*

| Incubation Time | No Barrier | KH₂PO₄ (15%) | Malonic Acid (10%) |
|---|---|---|---|
| *21 hours | False neg. on ADO +/− on GLU False pos. on CIT and MAL | Okay | Okay |
| *41 hours | False neg. on ADO False pos. on MAL | False pos. on MAL | Okay |
| *19½ hours | +/− on GLU and ADO False pos. on MAL, ARG, LYS, ORN and URE | Okay | Okay |
| *42 hours | +/− on ADO False pos. on MAL, ARG, LYS, ORN and URE | +/− on MAL | Okay |
| *19 hours | False neg. on ADO +/− on GLU False pos. on MAL, ARG, LYS, ORN and URE | Okay | Okay |
| *42 hours | +/− on ADO False pos. on MAL, ARG, LYS, | +/− on MAL | Okay |

TABLE XV-continued

Test organism - *providencia alcalifaciens*

| Incubation Time | No Barrier | KH₂PO₄ (15%) | Malonic Acid (10%) |
|---|---|---|---|
| *19½ hours | ORN and URE +/− on GLU and ADO False pos. on MAL, ARG, LYS, ORN and URE | Okay | Okay |
| *41 hours | False neg. on GLU and ADO False pos. on MAL, ARG, LYS, ORN and URE | +/− on MAL | Okay |

*These tests were conducted with the OF/G, ARG, ORN, LYS and URE wells oiled with mineral oil.

TABLE XVI

Test organism - *providencia alcalifaciens*

| Incubation Time | No Barrier | KH₂PO₄ (15%) | Oxalic Acid (9%) |
|---|---|---|---|
| *21 hours | False neg. on ADO +/− on GLU False pos. on CIT and MAL | Okay | Okay |
| *41 hours | False neg. on ADO False pos. on MAL | False pos. on MAL | Okay |

TABLE XVII

Test organism - *providencia alcalifaciens*

| Incubation Time | No Barrier | KH₂PO₄ (15%) | 5-Sulfosalicylic Acid 10% |
|---|---|---|---|
| *19½ hours | +/− on GLU and ADO False pos. on MAL, ARG, LYS, ORN and URE | Okay | False pos. on ARG, LYS and ORN |
| *42 hours | +/− on ADO False pos. on MAL, ARG, LYS, ORN and URE | +/− on MAL | Okay |

*These tests were conducted with the OF/G, ARG, ORN, LYS and URE wells oiled with mineral oil.

TABLE XVIII

Test organism - *providencia alcalifaciens*

| Incubation Time | No Barrier | KH₂PO₄ (15%) | Cysteine.HCl 10% |
|---|---|---|---|
| *19½ hours | +/− on GLU and ADO False pos. on MAL, ARG, LYS, ORN and URE | Okay | False pos. on ARG, LYS and ORN |
| *42 hours | +/− on ADO False pos. on MAL, ARG, LYS, ORN and URE | +/− on MAL | Okay |

TABLE XIX

| Incubation Time | Test organism - *providencia alcalifaciens* | | |
|---|---|---|---|
| | No Barrier | KH$_2$PO$_4$ (15%) | Glycine.HCl 10% |
| *19½ hours | +/− on GLU and ADO<br>False pos. on<br>MAL, ARG, LYS,<br>ORN and URE | Okay | Okay |
| *41 hours | False neg. on<br>GLU and ADO<br>False pos. on<br>MAL, ARG, LYS,<br>ORN and URE | +/− on MAL | Excess moisture<br>on strip<br>Acid drip into<br>wells |

*These tests were conducted with the OF/G, ARG, ORN, LYS and URE wells oiled with mineral oil.

TABLE XX

| Incubation Time | Test organism - *escherichia coli* | | |
|---|---|---|---|
| | No Barrier | KH$_2$PO$_4$ (15%) | Tartaric Acid 10% |
| *24 hours | False pos.<br>on CIT<br>and MAL | Okay | Okay |
| *42 hours | False neg.<br>on RHA<br>+/− on MAN<br>False pos. on<br>CIT and MAL | Okay | Okay |

TABLE XXI

| Incubation Time | Test organism - *escherichia coli* | | |
|---|---|---|---|
| | No Barrier | KH$_2$PO$_4$ (15%) | 5-Sulfosalicylic Acid 10% |
| *24 hours | False pos.<br>on CIT<br>and MAL | Okay | Okay |
| *42 hours | False neg.<br>on RHA<br>+/− on MAN<br>False pos. on<br>CIT and MAL | Okay | Okay |

TABLE XXII

| Incubation Time | Test organism - *escherichia coli* | | |
|---|---|---|---|
| | No Barrier | KH$_2$PO$_4$ (15%) | Oxalic Acid 9% |
| *24 hours | False pos.<br>on CIT<br>and MAL | Okay | Okay |
| *42 hours | False neg.<br>on RHA<br>+/− on MAN<br>False pos. on<br>CIT and MAL | Okay | Okay |

*These tests were conducted with the OF/G, ARG, ORN, LYS and URE wells oiled with mineral oil.

TABLE XXIII

| Incubation Time | Test organism - *escherichia coli* | | |
|---|---|---|---|
| | No Barrier | KH$_2$PO$_4$ (15%) | Citric Acid 10% |
| *24 hours | False pos.<br>on CIT<br>and MAL | Okay | Okay |
| *42 hours | False neg.<br>on RHA<br>+/− on MAN<br>False pos. on<br>CIT and MAL | Okay | Okay |

TABLE XXIV

| Incubation Time | Test organism - *escherichia coli* | | |
|---|---|---|---|
| | No Barrier | KH$_2$PO$_4$ (15%) | Potassium Acid Phthalate 8% |
| *24 hours | False pos.<br>on CIT<br>and MAL | Okay | False pos.<br>on MAL |
| *42 hours | False neg.<br>on RHA<br>+/− on MAN<br>False pos. on<br>CIT and MAL | Okay | False pos.<br>on CIT and MAL |

TABLE XXV

| Incubation Time | Test organism - *escherichia coli* | | |
|---|---|---|---|
| | No Barrier | KH$_2$PO$_4$ (15%) | MES Buffer 10% |
| *24 hours | False pos.<br>on CIT<br>and MAL | Okay | False pos.<br>on CIT<br>and MAL |
| *42 hours | False neg.<br>on RHA<br>+/− on MAN<br>False pos. on<br>CIT and MAL | Okay | False pos.<br>on CIT<br>and MAL |

*These tests were conducted with the OF/G, ARG, ORN, LYS and URE wells oiled with mineral oil.

TABLE XXVI

| Incubation Time | Test organism - *escherichia coli* | | |
|---|---|---|---|
| | No Barrier | KH$_2$PO$_4$ (15%) | Boric Acid 5% |
| *24 hours | False pos.<br>on CIT<br>and MAL | Okay | False pos.<br>on CIT<br>and MAL |
| *42 hours | False neg.<br>on RHA<br>+/− on MAN<br>False pos. on<br>CIT and MAL | Okay | False pos.<br>on CIT<br>and MAL |

TABLE XXVII

| Incubation Time | Test organism - *citrobacter freundii* | | |
|---|---|---|---|
| | No Barrier | KH$_2$PO$_4$ (15%) | Tartaric Acid 10% |
| *20 hours | False pos.<br>on ARG, LYS,<br>ORN and MAL | Okay | Okay |
| *41 hours | False neg.<br>on OF/G<br>False pos. on<br>ARG, LYS, ORN,<br>URE and MAL | Okay | Okay |

TABLE XXVIII

Test organism - *citrobacter freundii*

| Incubation Time | No Barrier | KH$_2$PO$_4$ (15%) | 5-Sulfosalicylic Acid 10% |
|---|---|---|---|
| *20 hours | False pos. on ARG, LYS, ORN and MAL | Okay | Okay |
| *41 hours | False neg. on OF/G False pos. on ARG, LYS, ORN, URE and MAL | Okay | +/− on GLU |

*These tests were conducted with the OF/G, ARG, ORN, LYS and URE wells oiled with mineral oil.

TABLE XXIX

Test organism - *citrobacter freundii*

| Incubation Time | No Barrier | KH$_2$PO$_4$ (15%) | Oxalic Acid 9% |
|---|---|---|---|
| *20 hours | False pos. on ARG, LYS, ORN and MAL | Okay | Okay |
| *41 hours | False neg. on OF/G False pos. on ARG, LYS, ORN, URE and MAL | Okay | False pos. on ARG, LYS and ORN |

TABLE XXX

Test organism - *citrobacter freundii*

| Incubation Time | No Barrier | KH$_2$PO$_4$ (15%) | Citric Acid 10% |
|---|---|---|---|
| *20 hours | False pos. on ARG, LYS, ORN and MAL | Okay | Okay |
| *41 hours | False neg. on OF/G False pos. on ARG, LYS, ORN, URE and MAL | Okay | Okay |

TABLE XXXI

Test organism - *citrobacter freundii*

| Incubation Time | No Barrier | KH$_2$PO$_4$ (15%) | Potassium Acid Phthalate 8% |
|---|---|---|---|
| *20 hours | False pos. on ARG, LYS, ORN and MAL | Okay | Okay |
| *41 hours | False neg. on OF/G False pos. on ARG, LYS, ORN, URE and MAL | Okay | +/− on ARA and RHA False pos. on MAL |

*These tests were conducted with the OF/G, ARG, ORN, LYS and URE wells oiled with mineral oil.

TABLE XXXII

Test organism - *citrobacter freuhdii*

| Incubation Time | No Barrier | KH$_2$PO$_4$ (15%) | MES Buffer 10% |
|---|---|---|---|
| *20 hours | False pos. on ARG, LYS, ORN and MAL | Okay | Okay |
| *41 hours | False neg. on OF/G False pos. on ARG, LYS, ORN, URE and MAL | Okay | False pos. on MAL |

TABLE XXXIII

Test organism - *citrobacter freundii*

| Incubation Time | No Barrier | KH$_2$PO$_4$ (15%) | Boric Acid 5% |
|---|---|---|---|
| *20 hours | False pos. on ARG, LYS, ORN and MAL | Okay | False pos. on MAL |
| *41 hours | False neg. on OF/G False pos. on ARG, LYS, ORN, URE and MAL | Okay on MAL | False pos. |

TABLE XXXIV

Test organism - *aeromonas caviae*

| Incubation Time | No Barrier | KH$_2$PO$_4$ (15%) | Tartaric Acid 10% |
|---|---|---|---|
| *20 hours | False pos. on LYS, ORN, URE, CIT and MAL | Okay | Okay |
| *41 hours | False pos. on LYS, ORN, URE, CIT and MAL | False pos. on CIT | False pos. on CIT |

*These tests were conducted with the OF/G, ARG, ORN, LYS and URE wells oiled with mineral oil.

TABLE XXXV

Test organism - *aeromonas caviae*

| Incubation Time | No Barrier | KH$_2$PO$_4$ (15%) | 5-Sulfosalicylic Acid 10% |
|---|---|---|---|
| *20 hours | False pos. on LYS, ORN, URE, CIT and MAL | Okay | Okay |
| *41 hours | False pos. on LYS, ORN, URE, CIT and MAL | False pos. on CIT | Okay |

TABLE XXXVI

Test organism - *aeromonas caviae*

| Incubation Time | No Barrier | KH$_2$PO$_4$ (15%) | Oxalic Acid 9% |
|---|---|---|---|
| *20 hours | False pos. on LYS, ORN, URE, CIT and MAL | Okay | Okay |
| *41 hours | False pos. on LYS, ORN, URE, CIT and MAL | False pos. on CIT | False pos. on CIT False neg. on ARG |

TABLE XXXVII

Test organism - *aeromonas caviae*

| Incubation Time | No Barrier | KH$_2$PO$_4$ (15%) | Citric Acid 10% |
|---|---|---|---|
| *20 hours | False pos. on LYS, ORN, URE, CIT and MAL | Okay | Okay |
| *41 hours | False pos. on LYS, ORN, URE, CIT and MAL | False pos. on CIT | False pos. on CIT |

*These tests were conducted with the OF/G, ARG, ORN, LYS and URE wells oiled with mineral oil.

TABLE XXXVIII

Test organism - *aeromonas caviae*

| Incubation Time | No Barrier | KH₂PO₄ (15%) | Potassium Acid Phthalate 8% |
|---|---|---|---|
| *20 hours | False pos. on LYS, ORN, URE, CIT and MAL | Okay | Okay |
| *41 hours | False pos. on LYS, ORN, URE, CIT and MAL | False pos. on CIT | False pos. on CIT and MAL |

TABLE XXXIX

Test organism - *aeromonas caviae*

| Incubation Time | No Barrier | KH₂PO₄ (15%) | MES Buffer 10% |
|---|---|---|---|
| *20 hours | False pos. on LYS, ORN, URE, CIT and MAL | Okay | Okay |
| *41 hours | False pos. on LYS, ORN, URE, CIT and MAL | False pos. on CIT | False pos. on CIT and MAL |

TABLE XXXX

Test organism - *aeromonas caviae*

| Incubation Time | No Barrier | KH₂PO₄ (15%) | Boric Acid 5% |
|---|---|---|---|
| *20 hours | False pos. on LYS, ORN, URE, CIT and MAL | Okay | False pos. on MAL |
| *41 hours | False pos. on LYS, ORN, URE, CIT and MAL | False pos. on CIT | False pos. on CIT and MAL |

*These tests were conducted with the OF/G, ARG, ORN, LYS and URE wells oiled with mineral oil.

TABLE XXXXI

Test organism - *pseudomonas aeruginosa*

| Incubation Time | No Barrier | KH₂PO₄ (15%) | KH₂PO₄ Plus 1% Gelatin |
|---|---|---|---|
| *19 hours | False neg. on GLU, ARA and MEL False pos. on LYS, ORN and URE | False pos. on LYS and ORN | False pos. on LYS and ORN |
| *42 hours | False neg. on GLU, ARA, and MEL False pos. on LYS, ORN and URE | False neg. on ARG | False neg. on GLU +/− on MEL False neg. on ARG False pos. on LYS and ORN |

*These tests were conducted with the OF/G, ARG, ORN, LYS and URE wells oiled with mineral oil.

TABLE XXXXII

Test organism - *pseudomonas aeruginosa*

| Incubation Time | No Barrier | KH₂PO₄ (15%) | Malonic Acid 10% |
|---|---|---|---|
| *19 hours | False neg. on GLU, ARA and MEL False pos. on LYS, ORN and URE | False pos. on LYS and ORN | False pos. on LYS and ORN |
| *42 hours | False neg. | False neg. | False neg. |

TABLE XXXXII-continued

Test organism - *pseudomonas aeruginosa*

| Incubation Time | No Barrier | KH₂PO₄ (15%) | Malonic Acid 10% |
|---|---|---|---|
| | on GLU, ARA, and MEL False pos. on LYS, ORN and URE | on ARG | on ARG False pos. on LYS |
| *19½ hours | False neg. on GLU, ARA and MEL False pos. on LYS, ORN and URE | False pos. on LYS and ORN | False pos. on LYS and ORN |
| *41 hours | False neg. on GLU, ARA, and MEL False pos. on LYS, ORN and URE | False pos. on LYS and ORN | False pos. on LYS and ORN |

*These tests were conducted with the OF/G, ARG, ORN, LYS and URE wells oiled with mineral oil.

TABLE XXXXIII

Test organism - *pseudomonas aeruginosa*

| Incubation Time | No Barrier | KH₂PO₄ (15%) | 10% Malonic Acid Plus 1% Gelatin |
|---|---|---|---|
| *19 hours | False neg. on GLU, ARA and MEL False pos. on LYS, ORN and URE | False pos. on LYS and ORN | False pos. on LYS and ORN |
| *42 hours | False neg. on GLU, ARA, and MEL False pos. on LYS, ORN and URE | False neg. on ARG | False neg. on GLU and ARG False pos. on LYS |

TABLE XXXXIV

Test organism - *pseudomonas aeruginosa*

| Incubation Time | No Barrier | KH₂PO₄ (15%) | Glycine.HCl 10% |
|---|---|---|---|
| *19½ hours | False neg. on GLU, ARA and MEL False pos. on LYS, ORN and URE | False pos. on LYS and ORN | False pos. on LYS and ORN |
| *41 hours | False neg. on GLU, ARA, and MEL False pos. on LYS, ORN and URE | False pos. on LYS and ORN | False neg. on GLU +/− on RHA False pos. on LYS and ORN |

*These tests were conducted with the OF/G, ARG, ORN, LYS and URE wells oiled with mineral oil.

TABLE XXXXV

Test organism - *proteus mirabilis*

| Incubation Time | No Barrier | KH₂PO₄ (15%) | 15% KH₂PO₄ Plus 1% Gelatin |
|---|---|---|---|
| *19 hours | False pos. on ARG, LYS and MAL | Okay | Okay |
| *42 hours | +/− on GLU and TRE False pos. on ARG, LYS | +/− on MAL | +/− on MAL |

TABLE XXXXV-continued

Test organism - proteus mirabilis

| Incubation Time | No Barrier | KH$_2$PO$_4$ (15%) | 15% KH$_2$PO$_4$ Plus 1% Gelatin |
|---|---|---|---|
| | | | and MAL |

TABLE XXXXVI

Test organism - proteus mirabilis

| Incubation Time | No Barrier | KH$_2$PO$_4$ (15%) | Malonic Acid 10% |
|---|---|---|---|
| *19 hours | False pos. on ARG, LYS and MAL | Okay | Okay |
| *42 hours | +/− on GLU and TRE False pos. on ARG, LYS and MAL | +/− on MAL | Okay |

TABLE XXXXVII

Test organism - proteus mirabilis

| Incubation Time | No Barrier | KH$_2$PO$_4$ (15%) | 10% Malonic Acid Plus 1% Gelatin |
|---|---|---|---|
| *19 hours | False pos. on ARG, LYS and MAL | Okay | Okay |
| *42 hours | +/− on GLU and TRE False pos. on ARG, LYS and MAL | +/− on MAL | Okay |

*These tests were conducted with the OF/G, ARG, ORN, LYS and URE wells oiled with mineral oil.

The preceding tests reveal the fact that boric acid, potassium acid phthalate, Bis-Tris buffer and Mes buffer are all unsuitable for use in treatment of the protective strips since each of them, while protecting some of the critical reactions, failed to protect others. I suspect that the two buffers, Bis-Tris buffer and Mes buffer both have pH ranges too high to provide adequate protection against the evolved alkaline gases under the conditions of these experiments. Boric acid, because of its low solubility in water, was used at the 15% (W/V) level for treating the paper strips and this could, perhaps, explain the low level of protection observed with some of the reactions.

The same sort of a solubility problem encountered with the boric acid also exists with potassium acid phthalate limiting its use to an 8% (W/V) concentration in water. Additionally, however, the relatively high pH (4.01) of the phthalic acid salt used to treat the strips when compared to potassium acid phosphate probably accounts for the significantly reduced protective action of the phthalate. Yet another factor is, of course, the significant difference in the molecular weights of these two acid salts (204 vs. 136) when comparing solutions of the same percentage concentration.

The paper strips impregnated with 5-sulfosalicylic acid provided adequate protection against the evolved alkaline products; however, as a practical matter, this acid proved to be too corrosive in that the barrier papers impregnated with it became brittle and essentially unusable after being stored for only a few months.

Glycine hydrochloride when used at a concentration of 10% (W/V) proved to be too hygroscopic. A high concentration of malonic acid (15%) also proved to be unsatisfactory for the same reason, i.e. excessive moisture take-up, when used as the impregnant and incubated for prolonged periods of time (40 to 42 hours). On the other hand, a 10% solution of malonic acid outperformed the potassium acid phosphate imprefnate even at the higher concentration of 15% (W/V) over extended incubation times of 40 to 42 hours in some of the reactions with some of the test organisms; whereas, during the shorter 18 to 22 hour incubation periods, the malonic acid and potassium acid phosphate impregnates showed little, if any significant differences.

All of the other compounds tested proved to be effective when used at concentrations of approximately 10% (W/V) including the oxalic acid at only 9%. Accordingly, oxalic acid, 5-sulfosalicylic acid, DL malic acid, DL tartaric acid and citric acid all proved effective at concentrations of around 10% (W/V). In addition to the forgoing list of polycarboxylic and sulfonated organic acids along with the previously tested inorganic acid phosphates, add cysteine hydrochloride, which, of course, is an acid salt of an amino acid. All of the above have proven to be satisfactory impregnates to protect the most significant of the critical reactions in the biochemical test wells of a microtiter test plate against cross contamination resulting from evolved alkaline gases.

What is claimed is:

1. The improved method for preventing cross-contamination of bacterial test wells in a multiple-well antimicrobial test plate wherein certain of the wells contain growing cultures of bacteria of the type that evolve alkaline gases, which comprises: covering the wells with a porous membrane dried after having been impregnated with an approximately 10% (W/V) solution of a solid water-soluble compound selected from the group consisting of inorganic acid phosphates, the acid salts of amino acids and the polycarboxylic organic acids which are relatively non-volatile, non-hygroscopic and non-toxic to humans and bacteria.

2. The improved method as set forth in claim 1 wherein the membrane is impregnated with an acid salt of an amino acid.

3. The improved method as set forth in claim 1 wherein the membrane is impregnated with a polycarboxylic organic acid.

4. The improved method as set forth in claim 1 in which the membrane is impregnated with cysteine hydrochloride.

5. The improved method as set forth in claim 1 in which the membrane is impregnated with a polycarboxylic acid selected from the group consisting of citric acid, oxalic acid, malonic acid, DL malic acid and DL tartaric acid.

* * * * *